(12) United States Patent
Boone et al.

(10) Patent No.: US 11,264,527 B2
(45) Date of Patent: Mar. 1, 2022

(54) INTEGRATED CIRCUIT PACKAGE AND SYSTEM USING SAME

(71) Applicant: Medtronic, Inc., Minneapolis, MN (US)

(72) Inventors: Mark R. Boone, Gilbert, AZ (US); Mark E. Henschel, Phoenix, AZ (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 16/148,702

(22) Filed: Oct. 1, 2018

(65) Prior Publication Data
US 2020/0105961 A1 Apr. 2, 2020

(51) Int. Cl.
| | | |
|---|---|---|
| H01L 25/16 | (2006.01) | |
| H01L 31/167 | (2006.01) | |
| H01L 25/075 | (2006.01) | |
| H01L 31/12 | (2006.01) | |
| H01L 33/00 | (2010.01) | |

(Continued)

(52) U.S. Cl.
CPC ........ *H01L 31/167* (2013.01); *H01L 25/0753* (2013.01); *H01L 25/165* (2013.01); *H01L 25/167* (2013.01); *H01L 31/12* (2013.01); *H01L 33/0093* (2020.05); *H01L 33/0095* (2013.01); *H01L 33/52* (2013.01); *H01L 33/62* (2013.01); *H01S 5/0201* (2013.01); *H01S 5/0237* (2021.01); *H01S 5/02208* (2013.01); *H01S 5/02234* (2021.01); *H01S 5/02325* (2021.01); *H01S 5/0425* (2013.01); *H01S 5/423* (2013.01); *A61B 5/0084* (2013.01); *A61B 2562/0238* (2013.01); *A61B 2562/182* (2013.01);

(Continued)

(58) Field of Classification Search
CPC .................................................... H01L 25/165
USPC ........................................................... 257/82
See application file for complete search history.

(56) References Cited

U.S. PATENT DOCUMENTS

| | | |
|---|---|---|
| 5,266,794 A | 11/1993 | Olbright et al. |
| 6,174,749 B1 | 1/2001 | Yuen et al. |

(Continued)

FOREIGN PATENT DOCUMENTS

| | | |
|---|---|---|
| EP | 3255686 | 12/2017 |
| WO | 2009143462 | 11/2009 |
| WO | 2018053378 | 3/2018 |

OTHER PUBLICATIONS

U.S. Appl. No. 15/477,904, filed Apr. 3, 2017, Boone.

(Continued)

*Primary Examiner* — Hsin Yi Hsieh
(74) *Attorney, Agent, or Firm* — Mueting Raasch Group (57) ABSTRACT

Various embodiments of an integrated circuit package and a method of forming such package are disclosed. The integrated circuit package includes first and second active dies. Each of the first and second active dies includes a top contact disposed on the top surface of the die and a bottom contact disposed on a bottom surface of the die. The package further includes a via die having first and second vias that each extends between a top contact disposed on a top surface of the via die and a bottom contact disposed on a bottom surface of the via die, where the bottom contact of the first active die is electrically connected to the bottom contact of the first via of the via die and the bottom contact of the second active die is electrically connected to the bottom contact of the second via of the via die.

20 Claims, 7 Drawing Sheets

(51) Int. Cl.
  *H01L 33/52* (2010.01)
  *H01L 33/62* (2010.01)
  *H01S 5/02* (2006.01)
  *H01S 5/02208* (2021.01)
  *H01S 5/042* (2006.01)
  *H01S 5/42* (2006.01)
  *H01S 5/0237* (2021.01)
  *H01S 5/02234* (2021.01)
  *H01S 5/02325* (2021.01)
  *A61B 5/00* (2006.01)

(52) U.S. Cl.
  CPC .................. *H01L 2933/005* (2013.01); *H01L 2933/0033* (2013.01); *H01L 2933/0066* (2013.01)

(56) References Cited

U.S. PATENT DOCUMENTS

| | | | |
|---|---|---|---|
| 6,259,121 B1 | 7/2001 | Lemoff et al. | |
| 6,636,544 B2 | 10/2003 | Baillargeon et al. | |
| 6,953,702 B2 | 10/2005 | Miller et al. | |
| 8,241,932 B1 | 8/2012 | Yu et al. | |
| 8,313,962 B2 | 11/2012 | Lott et al. | |
| 8,664,756 B2 | 3/2014 | Boone et al. | |
| 8,743,923 B2 | 6/2014 | Geske et al. | |
| 9,057,853 B2 | 6/2015 | Lau et al. | |
| 9,065,254 B2 | 6/2015 | Geske et al. | |
| 2008/0035935 A1 | 2/2008 | Shum | |
| 2011/0058372 A1* | 3/2011 | Lerman | H05K 1/0204 362/235 |
| 2015/0076529 A1 | 3/2015 | Wang et al. | |
| 2015/0129906 A1 | 5/2015 | Weigert | |
| 2020/0052466 A1* | 2/2020 | Chen | H01S 5/4043 |

OTHER PUBLICATIONS

Hunt et al., "Synergy between 2.5/3D Development and Hybrid 3D Wafer Level Fanout," *ASE Group Kaohsiung*, 10 pages.

Lin et al., "Advanced 3D eWLB-PoP (embedded Wafer Level Ball Grid Array—Package on Package) Technology," *2016 IEEE 66th Electronic Components and Technology Conference*, Singapore, 6 pages.

(PCT/US2019/053765) PCT Notification of Transmittal of the International Search Report and the Written Opinion of the International Searching Authority, dated Jan. 9, 2020, 12 pages.

* cited by examiner

INTEGRATED CIRCUIT PACKAGE AND SYSTEM USING SAME

BACKGROUND

IMDs for monitoring a physiological condition and/or delivering a therapy can include one or more physiological sensors. Such sensors can provide one or more signals related to one or more physiological conditions of a patient state. Examples of such IMDs include heart monitors, pacemakers, implantable cardioverter defibrillators (ICDs), myostimulators, neurological stimulators, drug delivery devices, insulin pumps, glucose monitors, etc.

A wide variety of electronic assemblies such as those that are utilized for IMDs employ electronic circuitry, e.g., for providing electrical stimulation of body tissue and/or monitoring a physiologic condition. Such IMDs may deliver electrical therapy energy in the form of shocking energy and stimulating pulses to selected body tissue. These IMDs typically include output circuitry for generating the electrical energy under prescribed conditions and at least one lead bearing a stimulation electrode for delivering the electrical energy to the selected tissue. For example, cardiac pacemakers and implantable cardioverter-defibrillators (ICDs) have been developed for maintaining a desired heart rate during episodes of bradycardia or for applying cardioversion or defibrillation therapies to the heart upon detection of serious arrhythmias. Other nerve, brain, muscle, and organ tissue stimulating medical devices are also known for treating a variety of conditions.

Currently available IMDs, including ICDs and implantable pulse generators (IPGs), are typically formed having a metallic housing that is hermetically sealed and, therefore, is impervious to body fluids, and a header or connector assembly mounted to the housing for making electrical and mechanical connection with one or more leads. Such devices also possess telemetry capabilities for communicating with external devices. Over the past several years, IMDs have evolved from relatively bulky devices to complex miniaturized devices that exhibit increasing functionality. For example, numerous improvements have been made in cardioversion/defibrillation leads and electrodes that have enabled the cardioversion/defibrillation energy to be precisely delivered to selected one or more portions of upper and lower heart chambers, thereby dramatically reducing the delivered shock energy required to cardiovert or defibrillate the heart chamber. High voltage output circuitry has also been improved to provide monophasic, biphasic, or multiphase cardioversion/defibrillation shock or pulse waveforms that are efficacious, sometimes with particular combinations of cardioversion/defibrillation electrodes, in lowering the required shock energy to cardiovert or defibrillate the heart.

Optical sensors may also be employed in IMDs as physiological sensors configured to detect changes in light modulation by, for example, a body fluid or tissue measurement volume due to a change in a physiological condition in the body fluid or tissue. Such optical sensors can be used, for example, to detect changes in metabolite levels in the blood, such as oxygen saturation levels or glucose levels, or changes in tissue perfusion. A typical optical sensor can include one or more light sources and one or more detectors that are adapted to detect light emitted by the light sources and modulated by, e.g., body fluid or tissue measurement volume.

Monitoring such physiological conditions provides useful diagnostic measures and may be used in managing therapies for treating a medical condition. For example, a decrease in blood oxygen saturation or in tissue perfusion may be associated with insufficient cardiac output or respiratory function. Thus, monitoring such conditions may allow an implantable medical device to respond to a decrease in oxygen saturation or tissue perfusion, for example, by delivering electrical stimulation therapies to the heart to restore a normal hemodynamic function.

SUMMARY

In general, the present disclosure provides various embodiments of an integrated circuit package and a method of forming such package. The package can include first and second active dies, where the first active die is adapted to emit electromagnetic radiation from a top surface that includes a first wavelength and the second active die is adapted to emit electromagnetic radiation from a top surface that includes a second wavelength different from the first wavelength. The package can also include a via die that includes first and second vias that each extend between a top contact disposed on a top surface of the via die and a bottom contact disposed on a bottom surface of the via die. A bottom contact of the first active die can be electrically connected to a bottom contact of the first via of the via die, and a bottom contact of the second active die can be electrically connected to a bottom contact of the second via of the via die.

In one aspect, the present disclosure provides an integrated circuit package that includes first and second active dies, where the first active die is adapted to emit electromagnetic radiation from a top surface that includes a first wavelength, and the second active die is adapted to emit electromagnetic radiation from a top surface that includes a second wavelength different from the first wavelength. Each of the first and second active dies includes a top contact disposed on the top surface of the die and a bottom contact disposed on a bottom surface of the die. The package further includes a via die having first and second vias that each extends between a top contact disposed on a top surface of the via die and a bottom contact disposed on a bottom surface of the via die, where the bottom contact of the first active die is electrically connected to the bottom contact of the first via of the via die, and the bottom contact of the second active die is electrically connected to the bottom contact of the second via of the via die.

In another aspect, the present disclosure provides a method of forming an integrated circuit package. The method includes disposing a patterned conductive layer on a major surface of an active die wafer; singulating the active die wafer to form a first active die and a second active die, where the first active die is adapted to emit electromagnetic radiation having a first wavelength, and the second active die is adapted to emit electromagnetic radiation having a second wavelength, where the first wavelength is different from the second wavelength; and disposing the first and second active dies on a carrier layer. The method further includes disposing a via die on the carrier layer; disposing an encapsulant over the first and second active dies, the via die, and the carrier layer to form a compression molded wafer comprising a top surface disposed on the carrier layer and a bottom surface; and removing the carrier layer from the compression molded wafer. The method further includes disposing one or more top contacts on a top surface of each of the first and second active dies and the via die; disposing a patterned conductive layer on the bottom surface of the compression molded wafer; and singulating the compression molded wafer to form an integrated circuit package that includes the first and second active dies and the via die.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

In this application, terms such as "a," "an," and "the" are not intended to refer to only a singular entity but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also, the recitations of numerical ranges by endpoints include all numbers subsumed within that range as well as the endpoints (e.g., 1 to 5 includes 1, 1.5, 2, 2.75, 3, 3.80, 4, 5, etc.).

These and other aspects of the present disclosure will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

Throughout the specification, reference is made to the appended drawings, where like reference numerals designate like elements, and wherein:

FIGS. 10A-J are various schematic cross-section views of one embodiment of a method of forming an integrated circuit package, where

DETAILED DESCRIPTION

In general, the present disclosure provides various embodiments of an integrated circuit package and a method of forming such package. The package can include first and second active dies, where the first active die is adapted to emit electromagnetic radiation from a top surface that includes a first wavelength and the second active die is adapted to emit electromagnetic radiation from a top surface that includes a second wavelength different from the first wavelength. The package can also include a via die that includes first and second vias that each extend between a top contact disposed on a top surface of the via die and a bottom contact disposed on a bottom surface of the via die. A bottom contact of the first active die can be electrically connected to a bottom contact of the first via of the via die, and a bottom contact of the second active die can be electrically connected to a bottom contact of the second via of the via die.

Typical integrated circuit packages (e.g., for memory to logic applications) include an embedded wafer level ball grid array package disposed on a similar package to provide a three-dimensional package-on-package device. The bottom die of the package-on-package device can be packaged utilizing a fan-out wafer level package process to form vias through the device that connect the top of the device to the bottom of the device. This allows the top package of the device to be placed on a top surface of the bottom package for interconnection to a die or dies of the bottom package and a printed circuit board on which the device is disposed. One issue with such three-dimensional package-on-package devices is that placement tolerances and relative movement during compression molding of the devices can be challenging to control.

The various embodiments of integrated circuit packages described herein can provide one or more advantages over current three-dimensional package-on-package devices. For example, in one or more embodiments, glass, silicon, or other encapsulating material can be utilized as die cavities and vias in a single structure. Such structure can render unnecessary tighter tolerances that are required for three-dimensional package-on-package devices. For one or more embodiments of integrated circuit packages described herein, the tolerance of a cavity to the via of the package will be determined by wafer fabrication capabilities and not determined by die level placement tolerances for package-on-package devices. Further, various embodiments of integrated circuit packages described herein can include two or more active dies that are each adapted to emit electromagnetic radiation of a given wavelength or wavelengths, where a first active die can emit a wavelength or wavelengths that are different from a wavelength or wavelengths emitted by a second active die.

The various embodiments of integrated circuit packages described herein can be utilized in any suitable electronic system. For example, one or more embodiments of integrated circuit packages described herein can be utilized in an IMD, ICD, IPG, insertable cardiac monitor, implantable diagnostic monitor, deep brain stimulator, implantable neurostimulator, injectable neurostimulator, implantable ventricular assist device, etc. In one or more embodiments, the integrated circuit packages described herein can be utilized in a wearable device or instrument that is external to a user's body.

Figure 1:
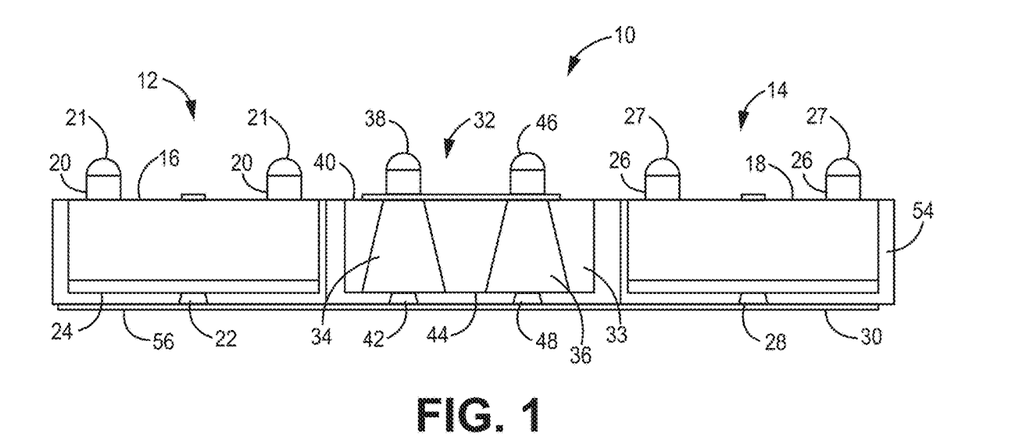
FIG. 1 is a schematic cross-section view of one embodiment of an integrated circuit package.
Figure 2:
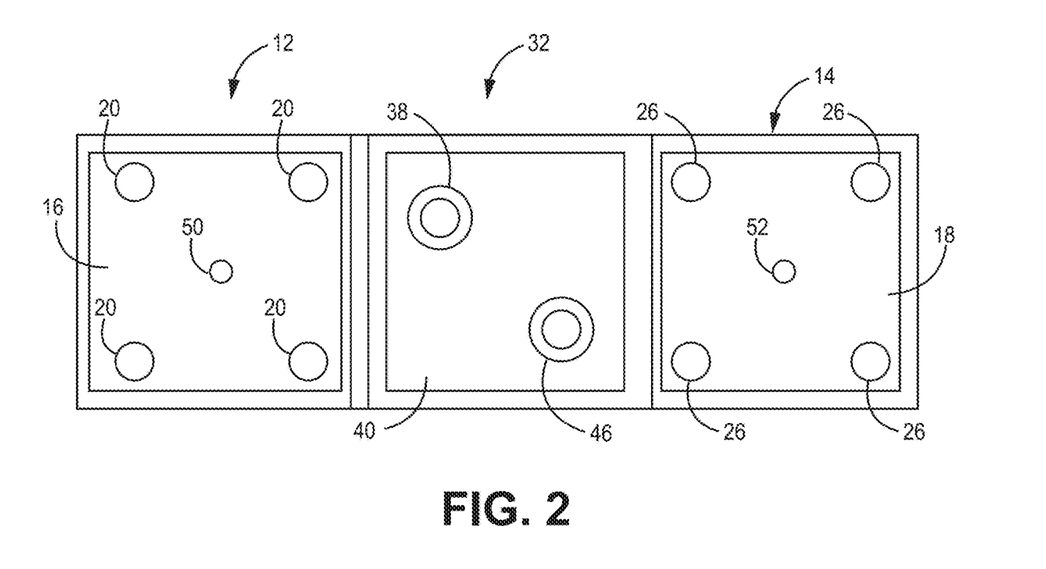
FIG. 2 is a schematic top plan view of the integrated circuit package of FIG. 1.

FIGS. 1-2 are various views of one embodiment of an integrated circuit package 10. The package 10 includes a first active die 12 and a second active die 14. The first active die 12 is adapted to emit electromagnetic radiation from a top surface 16 that includes a first wavelength. The second active die 14 is also adapted to emit electromagnetic radiation from a top surface 18 that includes a second wavelength different from the first wavelength. Further, the first active die 12 includes one or more top contacts 20 disposed on the top surface 16 of the die and one or more bottom contacts 22 disposed on a bottom surface 24 of the die, and the second active die 14 includes one or more top contacts 26 disposed on the top surface 18 of the die and one or more bottom contacts 28 disposed on a bottom surface 30 of the die.

The first integrated circuit package 10 also includes a via die 32 that has a first via 34 and a second via 36. The first via 34 extends between a top contact 38 disposed on a top surface 40 of the via die 32 and a bottom contact 42 disposed on a bottom surface 44 of the via die. Further, the second via 36 of the via die 32 extends between a top contact 46 disposed on the top surface 40 of the via die and a bottom contact 48 disposed on the bottom surface 44 of the via die. The bottom contact 22 of the first active die 12 is electrically connected to the bottom contact 42 of the first via 34 of the via die 32, and the bottom contact 28 of the second active die 14 is electrically connected to the bottom contact 48 of the second via 36 of the via die.

Each of the first and second active dies 12, 14 can include any suitable die or device, e.g., at least one of a capacitor, resistor, passive integrated capacitor system, logic circuit, analog circuit, diode, MOSFET, insulated-gate bipolar transistor, thyristor, light emitting diode, vertical-cavity surface-emitting laser, organic light emitting diode, etc. In one or more embodiments, at least one of the first and second active dies 12, 14 can be a light emitting die. For example, at least one of the first and second active dies 12, 14 can include any electrical circuit component(s) capable of emitting light in response to an applied voltage or current, including, for example, light emitting diodes (LEDs), laser diodes, vertical cavity surface emitting lasers (VCSELs), organic LEDs printed directly on the surface, nano-emitters, etc. Further, each of the first and second dies 12, 14 can be a cluster of one or more components that emit one or more discrete wavelengths or broadband emitters spanning a large range of wavelengths. Although depicted as including two dies 12, 14, the device 10 can include any suitable number of dies as is further described herein. In general, the number of active dies and corresponding emission wavelengths utilized in the packages described herein can be selected according to the requirements of a particular application and will depend on the physiological condition or conditions being monitored.

The first active die 12 is adapted to emit electromagnetic radiation from the top surface 16, and the second active die 14 is adapted to emit electromagnetic radiation form the top surface 18. In other words, the top surfaces 16, 18 of the first and second active dies 12, 14 are emitting surfaces. Although depicted as having one emitting surface 16, 18, each of the first and second active dies 12, 14 can include two or more emitting surfaces.

At least one of the first and second active dies 12, 14 can be a packaged light source. In one or more embodiments, at least one of the first and second active dies 12, 14 can include a flip-chip type package. In one or more embodiments, at least one of the first and second active dies 12, 14 can be a bare semiconductor die.

The first and second active dies 12, 14 can be adapted to emit electromagnetic radiation of any suitable wavelength or wavelengths. In one or more embodiments, the first and second active dies 12, 14 can emit at least one of infrared, near-infrared, visible, and UV light. In one or more embodiments, the first and second active dies 12, 14 can emit visible light having a wavelength of at least 350 nm and no greater than 950 nm. The first and second active dies 12, 14 can emit any suitable bandwidth of electromagnetic radiation. In one or more embodiments, the first and second active dies 12, 14 can emit electromagnetic radiation in a narrow band, e.g., the dies are adapted to emit light having an emission bandwidth no greater than 20 nm, 15 nm, 10 nm, or 5 nm full-width at half-maximum (FWHM). In one or more embodiments, a narrow band emitting active die can be paired with a broadband detector that is sensitive to all wavelengths emitted by the die. In one or more embodiments, a narrow-band emitting active die can be paired with a narrow-band detector. Further, in one or more embodiments, a narrow band emitting active die can be paired with two or more broadband detectors. For example, silicon detectors can be sensitive in the visible to near-infrared wavelength ranges (e.g., up to about 1000 nm), but gallium arsenide can be sensitive to longer infrared wavelengths (e.g., greater than 1000 nm). In one or more embodiments, a broadband emitting active die can be utilized with two or more narrow band detectors.

In one or more embodiments, each of the first and second active dies 12, 14 can include a broadband emitter that utilizes re-emission of phosphorous materials or combination of broadband FWHM LEDs, e.g., a 680 nm LED with greater than a 50 nm FWHM that spans into the 720 nm wavelength. In such embodiments, a single LED can provide emission at both 680 nm and 720 nm, paired with a detector that can discriminate between these two wavelengths. Similarly, a second broadband FWHM die can be used at 800 nm that also spans 760 nm. In such embodiments, two broadband FWHM dies can span four wavelengths, e.g., 680, 720, 760, and 800 nm.

In one or more embodiments, the first active die 12 can be adapted to emit electromagnetic radiation from the top surface 16 that includes a first wavelength or wavelength band and the second active die 14 can be adapted to emit electromagnetic radiation from the top surface 18 that includes a second wavelength or wavelength band. In one or more embodiments, the first wavelength is the same as the second wavelength. Further, in one or more embodiments, the first wavelength is different from the second wavelength.

In one or more embodiments, at least one of the first and second active dies 12, 14 can be adapted to emit electromagnetic radiation in one or more pulses having any suitable pulse width and periodicity. Further, in one or more embodiments, at least one of the first and second active dies 12, 14 may be pulsed in a sequential manner.

At least one of the first and second active dies 12, 14 can have any suitable cone angle of emission. As used herein, the term "cone angle" refers to solid angle relative to a normal to an emitting surface (e.g., top surface) of the die. In one or more embodiments, at least one of the first and second active dies 12, 14 can have a cone angle of no greater than 90 degrees, 80 degrees, 70 degrees, 60 degrees, 50 degrees, 40 degrees, 30 degrees, 20 degrees, 10 degrees, or 5 degrees. In one or more embodiments, at least one of the first and second active dies 12, 14 can emit electromagnetic radiation hemispherically from its respective top surface 16, 18.

The first active die 12 includes one or more top contacts 20 disposed on the top surface 16 of the die. As seen in FIG. 2, the first active die 12 includes four top contacts 20. The first active die 12 can include any suitable number of top contacts, e.g., one, 2, 3, 4, 5, or more top contacts. The top contacts 20 can include any suitable contact or pad that can provide an electrical connection to the active die 12. In one or more embodiments, one or more of the top contacts 20 can include a conductive pillar (or a solder bump with a barrier metal disposed over a die pad) that can be disposed on the top surface 16 of the active die 12 using any suitable technique or techniques, e.g., electroplating, etching, photo etching, ablation, laser ablation, etc. Further, the top contacts 20 can each include a solder bump 21 disposed thereon any suitable solder bumps 21 can be disposed on the top contacts 20. The top contacts 20 can have any suitable dimensions and can be disposed in any suitable arrangement or array on the top surface 16 of the first active die 12. Further, the top contacts 20 can include any suitable conductive material or materials.

The second active die 14 also includes one or more top contacts 26 disposed on the top surface 18 of the die. The top contacts 26 of the second active die 14 can include any suitable contacts or conductive pads described here in, e.g., the same conductive contacts as top contacts 20 of first active die 12. All of the design considerations and possibilities regarding the top contacts 20 of the first active die 12 apply equally to the top contacts 26 of the second active die 14. In one or more embodiments, the top contacts 26 of the second active die 14 can each include a solder bump 27 disposed on one or more of the top contacts.

The first active die 12 also includes one or more bottom contacts 22 disposed on the bottom surface 24 of the first active die, and the second active die 14 also includes one or more bottom contacts 28 disposed on the bottom surface 30 of the second active die. The bottom contacts 22, 28 are adapted to provide an electrical connection to the first and second active dies 12, 14 respectively. The bottom contacts 22, 28 of the first and second active dies 12, 14 can include any suitable contact or conductive pad described herein regarding top contacts 20, 26. Further, the bottom contacts 22, 28 can have any suitable dimensions and be disposed in any suitable arrangement or array on the bottom surfaces 24, 30 of the first and second of active dies 12, 14 respectively. Further, the bottom contacts 22, 28 can take any suitable shape or shapes.

Although not shown in FIGS. 1-2, one or more top contacts 20 of the first active die 12 can be electrically connected to one or more top contacts 26 of the second active die 14 using any suitable technique or techniques.

Further, for example, the bottom contacts 22, 28 of the first and second active dies 12, 14 can be electrically connected to bottom contacts 42, 48 of the via die 32 using any suitable technique or techniques.

The integrated circuit package 10 also includes the via die 32. The via die 32 includes the first via 34 and the second via 36. Although depicted as including first and second vias 34, 36, the via die 32 can include any suitable number of vias, e.g., 1, 2, 3, 4, 5, or more vias. The via die 32 can include any suitable material or materials, e.g., glass, quartz, sapphire, ceramic, high temperature plastic, printed wiring board material, polyimide flex tape, etc.

The first via 34 extends between the top contact 38 disposed on the top surface 40 of the via die 32 and the bottom contact 42 disposed on the bottom surface 44 of the die. Further, the second via 36 extends between the top contact 46 disposed on the top surface 40 of the via die 32 and the bottom contact 48 disposed on the bottom surface 44 of the die. The vias 34, 36 can include any suitable conductive material or materials and be formed using any suitable technique or techniques. For example, in one or more embodiments, one or more openings can be formed through a die body 33 of the via die 32, and conductive material can be disposed in the openings to form the vias 34, 36. Such openings can take any suitable shape or shapes. Further, the top contacts 38, 46 of the vias 34, 36 can be disposed on the top surface 40 such that they are electrically connected to the vias using any suitable technique or techniques. And the bottom contacts 42, 48 of the first and second vias 34, 36 can be disposed on the bottom surface 44 of the via die 32 such that they are electrically connected to the vias using any suitable technique or techniques.

As mentioned herein, the first and second active dies 12, 14 are adapted to emit electromagnetic radiation from at least the top surfaces 16, 18 of the respective dies. Each active die 12, 14 can emit electromagnetic radiation from any portion or portions of the respective top surface 16, 18. In one or more embodiments, the first die 12 can include an aperture 50, and the second die 14 can include an aperture 52 as shown in FIG. 2. Each of the first and second active dies 12, 14 are adapted to emit electromagnetic radiation through its respective aperture 50, 52. These apertures 50, 52 can be formed using any suitable technique or techniques. In one or more embodiments, a masking layer or layers can be disposed on the top surfaces 16, 18 of the first and second active dies 12, 14, and the apertures 50, 52 can be formed in the masking layer using any suitable technique or techniques. The masking layer can include any suitable number of layers. Further, the masking layer can include any suitable material or materials, e.g., polymeric, metallic, inorganic materials, and combinations thereof. In one or more embodiments, the masking layer can include a dielectric material. In one or more embodiments, the masking layer can include an electrically conductive material. In one or more embodiments, the masking layer can include an absorbing material such that the layer is adapted to absorb electromagnetic radiation having any suitable wavelength or range of wavelengths, e.g., one or more of ultraviolet, visible, near infrared, and infrared light. Suitable materials for the masking layer include TiN, fractal TiN, titanium, etc.

If the masking layer includes electrically conductive materials, then an optional insulating layer can be disposed between the masking layer and one or more conductors disposed on the top surfaces 16, 18 of the first and second active dies 12, 14. The insulating layer can include any suitable material or materials that insulate the masking layer from the conductor, e.g., siloxane, silicon nitride, etc. In one or more embodiments, the insulating layer includes a dielectric material.

The masking layer can be disposed on any suitable portion or portions of the top surfaces 16, 18 of the first and second active dies 12, 14 using any suitable technique or techniques. In one or more embodiments, the masking layer can be disposed on the top surfaces 16, 18 using, e.g., plasma vapor deposition, chemical vapor deposition, physical vapor deposition, etc., followed by photolithography, chemical etching, etc.

Figure 3:
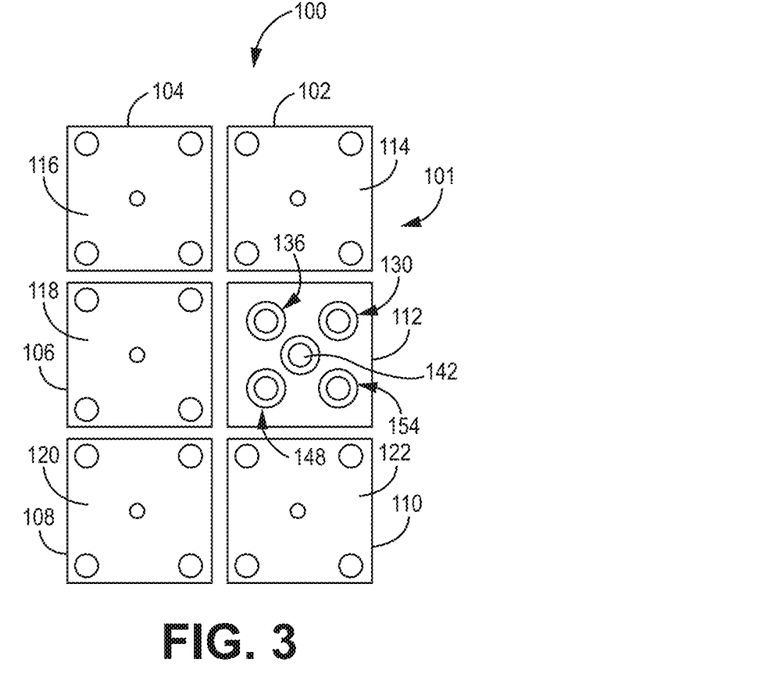
FIG. 3 is a schematic top plan view of another embodiment of an integrated circuit package.
Figure 4:
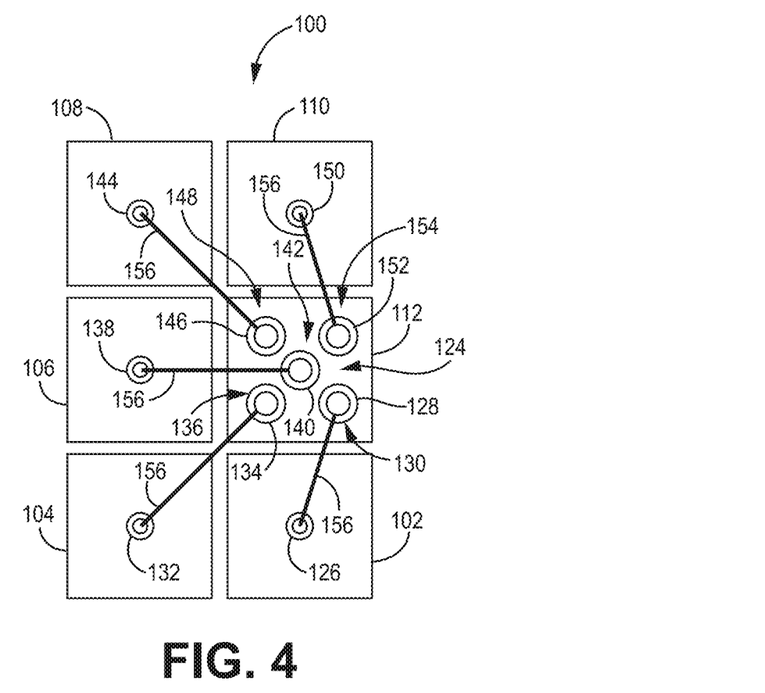
FIG. 4 is a schematic bottom plan view of the integrated circuit package of FIG. 3.

Any suitable technique or techniques can be utilized to electrically connect one or more bottom contacts 22, 28 of the first and second active dies 12, 14 to one or more bottom contacts 42, 48 of the via die 32. For example, FIGS. 3-4 are various schematic views of another embodiment of an integrated circuit package 100. All of the design considerations and possibilities regarding the integrated circuit package 10 of FIGS. 1-2 apply equally to the integrated circuit package 100 of FIGS. 3-4. Integrated circuit package 100 includes first, second, third, fourth, and fifth active dies 102, 104, 106, 108, 110 (collectively referred to as active dies 101) and a via die 112.

One difference between the integrated circuit package 100 of FIGS. 3-4 and the integrated circuit package 10 of FIGS. 1-2 is that package 100 includes five active dies 101 that can be arranged in any suitable arrangement or array along with the via die 112. Each of the active dies 101 are adapted to emit electromagnetic radiation from one or more surfaces of the die. For example, in one or more embodiments, active die 102 can be adapted to emit electromagnetic radiation that includes a first wavelength or wavelength band from a top surface 114, active die 104 can be adapted to emit electromagnetic radiation that includes a second wavelength or wavelength band from a top surface 116, the third active die 106 can be adapted to emit electromagnetic radiation that includes a third wavelength or wavelength band from a top surface 118, the fourth active die 108 can be adapted to emit electromagnetic radiation that includes a fourth wavelength or wavelength band from a top surface 120, and the fifth active die 110 can be adapted to emit electromagnetic radiation that includes a fifth wavelength or wavelength band from a top surface 122.

Further, as shown in FIG. 4, a bottom contact of one or more of the active dies 101 can be electrically connected to one or more bottom contacts 124 of the via die 112 using any suitable technique or techniques. In one or more embodiments, bottom contact 126 of the first active die 102 is electrically connected to bottom contact 128 of a first via 130 using any suitable technique or techniques. For example, one or more conductors 156 can be disposed on or above bottom surfaces of the active dies 101 that electrically connect the bottom contact 126 of the first active die 102 to the bottom contact 128 of the first via 130 of the via die 112. Further, bottom contact 132 of the second active die 104 is electrically connected to bottom contact 134 of a second via 136 of the via die 112, bottom contact 138 of the third active die 106 is electrically connected to bottom contact 140 of a third via 142 of the via die, bottom contact 144 of the fourth active die 108 is electrically connected to bottom contact 146 of a fourth via 148 of the via die, and bottom contact 150 of the fifth active die 110 is electrically connected to bottom contact 152 of a fifth via 154 of the via die.

In one or more embodiments, the bottom contact of one or more active dies 101 can be electrically connected to one or more bottom contacts 124 of the via die 112 by utilizing a photolithographic technique to pattern conductive segments that connect the bottom surface of the active die 101 to a bottom contact 124 of the via die 112. In one or more embodiments, a patterned conductive epoxy layer can be disposed on the bottom surface of the package 100 using any suitable technique or techniques. Further, in one or more embodiments, a trace pattern can be patterned on the bottom surface of the package 100 using any suitable technique or techniques, e.g., printing, photolithography, etc., to electrically connect the bottom contact of one or more active dies 101 to one or more bottom contacts 124 of the via die 112.

Returning to FIGS. 1-2, the first and second active dies 12, 14 and the via die 32 can be disposed in any suitable arrangement or array. Further, one or more of the dies 12, 14, 32 can be in contact with each other or spaced apart any suitable distance. In one or more embodiments, the first and second active dies 12, 14 and the via die 32 can be disposed on a substrate or carrier using any suitable technique or techniques. Any suitable substrate or carrier can be utilized. In one or more embodiments, a patterned conductive layer 56 can be disposed on the bottom surfaces 24, 30, 44 of the dies 12, 14, 32 that electrically connects the bottom contact 22 of the first active die to the bottom contact 42 of the first via 34 of the via die. Further, the patterned conductive layer 56 can also electrically connect the bottom contact 28 of the second active die 14 to the bottom contact 48 of the second via 36 of the via die 32. Any suitable technique or techniques can be utilized to dispose the patterned conductive layer 56 on the bottom surfaces 24, 30, 44 of the dies 12, 14, 32. In one or more embodiments, the patterned conductive layer can include one or more wires or conductors that electrically connect the bottom contact 22 of the first active die 12 to the bottom contact 42 of the first via 34 of the via die 32 and the bottom contact 28 of the second active die 14 to the bottom contact 48 of the second via 36 of the via die 32.

In one or more embodiments, the first and second active dies 12, 14 and the via die 32 can be disposed in a molded encapsulant 54. The molded encapsulant 54 can include any suitable material or materials, e.g., a thermosetting epoxy resin that includes organic or inorganic (e.g., silica) filler particles, an epoxy film that is laminated to the first and second active dies 12, 14, etc. Further, the dies 12, 14, 32 can be disposed in the encapsulant 54 using any suitable technique or techniques as is further described herein. In one or more embodiments, the encapsulant 54 is disposed between the first and second active dies 12, 14 and the via die 32.

The various embodiments of integrated circuit packages described herein can be utilized in any suitable device or system, e.g., the devices described in U.S. patent application Ser. No. 15/477,904, filed Apr. 3, 2017, and entitled HERMETICALLY-SEALED PACKAGE AND METHOD OF FORMING SAME. For example, FIGS. 5-9 are various schematic views of one embodiment of a hermetically-sealed system 200. The system 200 includes a housing 202 and a substrate 204. The housing 202 includes an inner surface 206 and an outer surface 208. The substrate 204 can be a non-conductive substrate and includes a first major surface 210 and a second major surface 212. The package 200 can also include one or more electronic devices 214 disposed within the housing 202. For example, the electronic devices 214 can include the integrated circuit package 10 of FIGS. 1-2. Although depicted as including integrated circuit package 10, the system 200 can include any suitable integrated circuit package. In one or more embodiments, the integrated circuit package 10 can be disposed on the first major surface 210 of the substrate 204. The integrated circuit package 10 can be adapted to transmit at least a portion of the electromagnetic radiation emitted by each of the first and second actives dies 12, 14 through the first and second major surfaces 210, 212 of the substrate 204.

Figure 7:
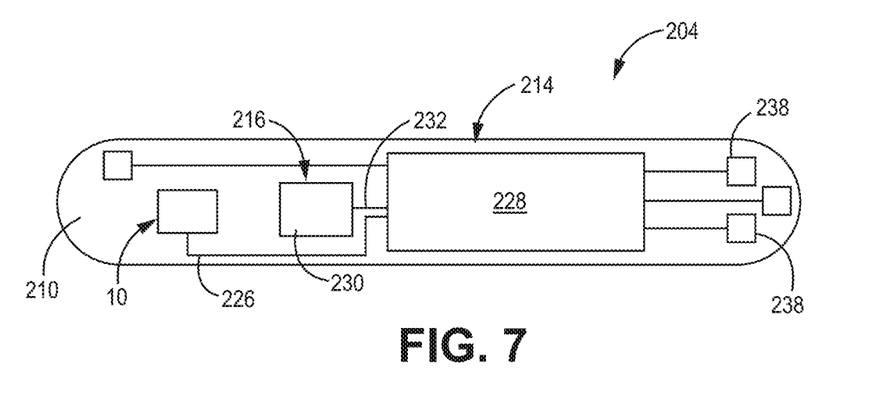
FIG. 7 is a schematic bottom plan view of a substrate of the hermetically-sealed system of FIG. 5.
Figure 8:
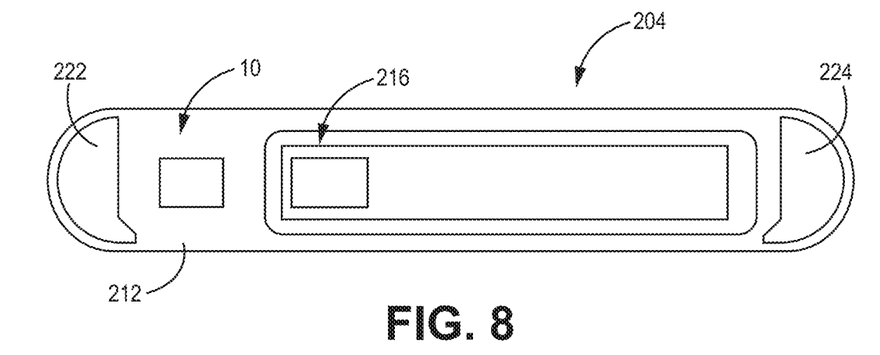
FIG. 8 is a schematic top plan view of the substrate of the hermetically-sealed system of FIG. 5.

The electronic devices 214 can further include a detector 216 (FIG. 7). In one or more embodiments, the detector 216 can be disposed on the first major surface 210 of the substrate 204. In one or more embodiments, one or more detectors can be disposed on the second major surface 212 of the substrate 204. In one or more embodiments, one or more detectors can be disposed on each of the first and second major surfaces 210, 212 of the substrate 204. The detector 216 can be adapted to detect at least a portion of the electromagnetic radiation transmitted through the first and second major surfaces 210, 212 of the substrate 204 by the first and second active dies 12, 14 of the integrated circuit package 10. For example, in one or more embodiments, the detector 216 can be adapted to detect at least a portion of the electromagnetic radiation emitted by the integrated circuit package 10 and transmitted through the substrate 204 such that it is scattered by a volume (not shown) of tissue within a patient adjacent the second major surface 212 of the substrate 204 and directed through the second major surface and then the first major surface 210 to the detector. Together, the integrated circuit package 10 and the detector 216 can, in one or more embodiments, provide an optical sensor.

Figure 5:
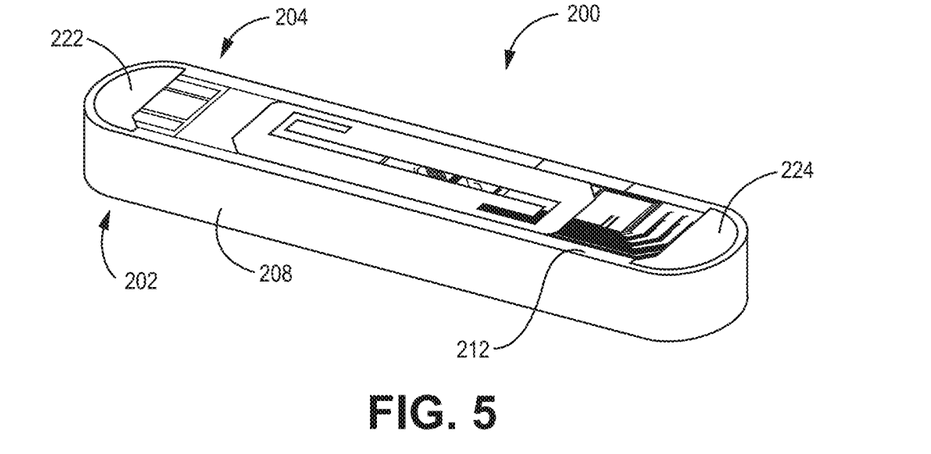
FIG. 5 is a schematic perspective view of one embodiment of hermetically-sealed system that includes the integrated circuit package of FIG. 1.
Figure 6:
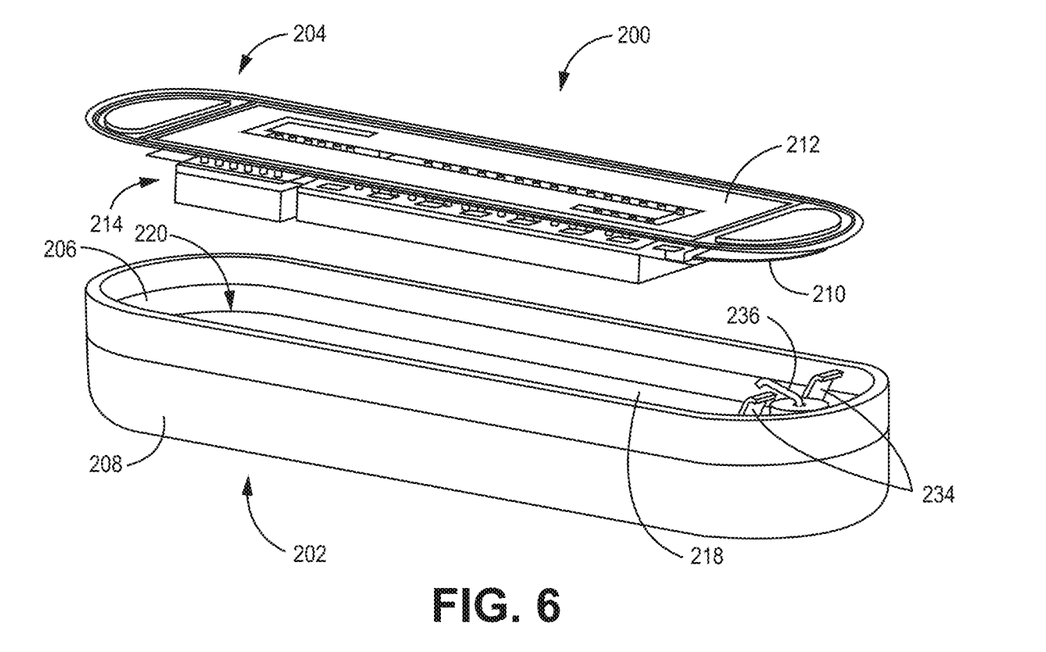
FIG. 6 is a schematic exploded view of the hermetically-sealed system of FIG. 5.

The package 200 also includes a power source 218 that is disposed at least partially within the housing 202. In one or more embodiments, the power source 218 can be disposed within a cavity 220 of the housing 202. The power source 218 can include any suitable power source or sources as is further described herein. Further, the power source can be electrically connected to the electronic devices 214 using any suitable technique or techniques. For example, in one or more embodiments, the power source 218 can include one or more power sources contacts 234, 236 can be electrically connected to one or more device contacts 238 when the substrate 204 is sealed to the housing 202 using any suitable technique or techniques.

The substrate 204 can be sealed to the housing 202. In one or more embodiments, the substrate 204 can be hermetically sealed to the housing 202. The substrate 204 can be sealed to the housing 202 using any suitable techniques or techniques. In one or more embodiments, the substrate 204 can be hermetically sealed to the housing 202 by a laser bond.

The housing 202 can include any suitable material or materials, e.g., metallic, polymeric, ceramic, or inorganic materials. In one or more embodiments, the housing 202 can include at least one of glass, quartz, silica, sapphire, silicon carbide, titanium, and diamond. In one or more embodiments, the housing 202 can include at least one of copper, silver, titanium, niobium, zirconium, tantalum, stainless steel, platinum, and iridium. The housing 202 can include the same material or combination of materials as the substrate 204. In one or more embodiments, the housing 202 can include one or more materials that are different from the material or materials of the substrate 204. Further, in one or more embodiments, the housing 202 can include biocompatible materials such that the system 200 can be implanted within a patient's body. For example, one or more coatings or layers can be disposed on the outer surface 208 of the housing 202 that provide biocompatibility. In one or more embodiments, the housing 202 can be electrically conductive to provide a ground electrode for the system 200 as is known in the art. In one or more embodiments, the housing 202 can be nonconductive.

Further, the housing 202 can take any suitable shape or shapes and can have any suitable dimensions. In one or more embodiments, the housing 202 takes a shape that forms the cavity 220 that can accommodate the power source 218 (including active material and power source electronics) and one or more electronic devices 214 as is further described herein.

Sealed to the housing 202 is the substrate 204. In one or more embodiments, the substrate 204 can be a non-conductive or dielectric substrate such that the electronic devices 214 (including integrated circuit package 10 and detector 216), optional external electrodes 222, 224 and any conductors or other devices disposed on the substrate can be electrically isolated if desired. The substrate 204 can include any suitable material or materials. In one or more embodiments, the substrate 204 can include at least one of glass, quartz, silica, sapphire, silicon carbide, diamond, and gallium nitride. As with the housing 202, the substrate 204 can include a biocompatible material. For example, the substrate 204 can include one or more coatings or layers that can provide biocompatibility.

In one or more embodiments, the substrate 204 can be a transparent substrate. As used herein, the phrase "transparent substrate" refers to a substrate that can transmit a given percentage of light incident thereon during use of laser bonding techniques described herein to preferentially heat only an outer surface of the substrate (e.g., first major surface 210 or second major surface 212 of substrate 204), and not an inner bulk of the substrate, and thereby create a bond that has a relatively greater strength than the bulk strength of the substrate. Further, the transparent substrate 204 can transmit light emitted by the integrated circuit package 10 having any suitable wavelength or combinations of wavelengths. The substrate 204 can be substantially transparent at a desired wavelength or range of wavelengths. As used herein, the phrase "substantially transparent" means that the substrate 204 transmits greater than 50% of light incident on the substrate for a selected wavelength or range of wavelengths, assuming no reflection at the air-substrate boundaries. In one or more embodiments, the substrate 204 can be substantially transmissive to light having a wavelength of at least 200 nm. In one or more embodiments, the substrate 204 can be substantially transmissive to light having a wavelength of greater than 10,000 nm. In one or more embodiments, the substrate 204 can be substantially transmissive to light having a wavelength in a range of 200 nm to 10,000 nm. In one or more embodiments, the substrate 204 can be substantially transmissive to at least one of UV light, visible light, and IR light.

In one or more embodiments, at least a portion of the substrate 204 can be transparent such that the detector 216 disposed on the first major surface 210 can detect one or more external signals, e.g., from a patient, when the system 200 is disposed within the patient. In one or more embodiments, the at least a portion of the substrate 204 can be sufficiently transparent to enable transmission of all, or a sufficient magnitude, of the light that is incident on the substrate for reception by the detector 216 such that the received light can be processed to detect the external signal. In one or more embodiments, the substrate 204 can be opaque, and a through-hole can be formed through the substrate and filled with a transparent hermetic material such as glass to provide a transparent portion of the substrate.

The substrate 204 can include any suitable dimensions, e.g., thicknesses. Further, the substrate 204 can take any suitable shape or combinations of shapes. In one or more embodiments, the substrate 204 can take a shape or combination of shapes that is complementary to a shape of the housing 202 such that the substrate can be sealed to the housing and provide a low-profile shape for the system 200.

Further, the substrate 204 can be a single, unitary substrate or multiple substrates joined together.

Disposed on the first major surface 210 of the substrate 204 are the electronic devices 214. Although depicted as being disposed on the first major surface 210, one or more electronic devices 214 can be disposed on the second major surface 212, or one or more electronic devices can be disposed on both the first and second major surfaces. In one or more embodiments, one or more electronic devices 214 can be disposed within the housing 204 and not connected to the substrate 202. The electronic devices 214 can include any suitable circuit or component, e.g., capacitors, transistors, integrated circuits, including controllers and multiplexers, sensors, light sources, detectors, accelerometers, signal processors, etc.

Further, any suitable technique or combination of techniques can be utilized to dispose one or more electronic devices 214 on the substrate 204 and/or within the cavity 220 of the housing 202. In one or more embodiments, one or more electronic devices 214 can be formed on the first major surface 210 of the substrate 204. In one or more embodiments, one or more devices 214 can be formed separately and then attached to the first major surface 210. Any suitable technique or techniques can be utilized to attach the electronic devices 214 to the substrate 204, e.g., a bond can be formed between the electronic device and the first major surface 210 of the substrate. The electronic devices 214 can include one or more integrated circuit packages 10 each having any suitable number of active dies.

Figure 9:
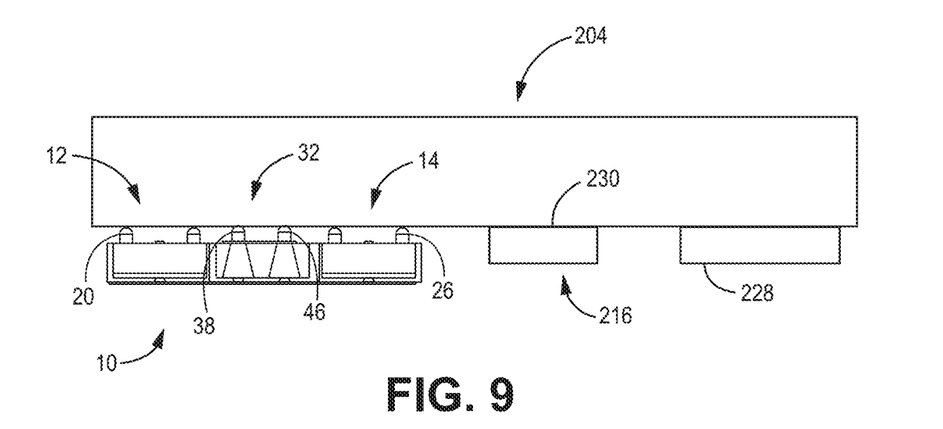
FIG. 9 is a schematic cross-section view of the substrate of the hermetically-sealed system of FIG. 5.

The integrated circuit package 10 can be disposed in any suitable location within the housing 202 of the system 200. In one or more embodiments, the integrated circuit package 10 is disposed adjacent the first major surface 210 of the substrate 204. As used herein, the term "adjacent" means that an element or component is disposed closer to the first major surface 210 of the substrate 204 than to the power source 218 disposed within the housing 202. In one or more embodiments, the integrated circuit package 10 can be disposed on the first major surface 210 of the substrate 204 as shown in FIG. 9 using any suitable technique or techniques. In such embodiments, one or more top contacts 20 of the first active die 12, top contacts 26 of the second active die 14, and top contacts 38, 46 of the via die 32 of the integrated circuit package 10 can be connected to one or more conductors 226 (FIG. 7) disposed on the first major surface 210 of the substrate 204 using any suitable technique or techniques, e.g., bump bonding, solder reflow, conventional wire bonding, laser ribbon bonding, conductive epoxy bonding, etc.

The integrated circuit package 10 can be electrically connected to one or more electronic devices 214 disposed on one or both of the first major surface 210 and second major surface 212 of the substrate 204 or within the housing 202 using any suitable technique or techniques. For example, the integrated circuit package 10 can be electrically connected to the conductor 226 (FIG. 7) that is disposed on or within the substrate 204. The conductor 226 can electrically connect the integrated circuit package 10 to a controller 228 of the electronic devices 214. In one or more embodiments, a patterned conductive layer (not shown) can be disposed on the first major surface 210 of the substrate 204. In such embodiments, the first and second active dies 12, 14 and the via die 32 of the integrated circuit package 10 can be electrically connected to the patterned conductive layer disposed on the first major surface 210 of the substrate 204 using any suitable technique or techniques.

The system 200 also includes the detector 216. The detector 216 includes a detecting surface 230 (FIG. 9). The detector 216 can include any suitable detector that is adapted to detect light emitted by the integrated circuit package 10, e.g., one or more photodiodes, photoresistors or light dependent resistors, phototransistors, photovoltaic cells, charge-coupled devices, avalanche detectors, etc. In one or more embodiments, the integrated circuit package 10 can also be utilized as a detector. Although depicted as including a single detector 216, the system 200 can include any suitable number of detectors. For example, the system 200 can include a second detector (not shown) disposed on the first major surface 210 of the substrate 204. In one or more embodiments, the detector 216 can be adapted to detected electromagnetic radiation emitted by the first active die 12 of the integrated circuit package 10 and the second detector is adapted to detected electromagnetic radiation emitted by the second active die 14 of the integrated circuit package.

The detector 216 can be adapted to detect any desired wavelength or wavelengths of electromagnetic radiation. In one or more embodiments, the detector 216 can detect one or more of infrared, near-infrared, visible, and UV light. In one or more embodiments, the detector 216 can detect visible light having a wavelength of at least 350 nm and no greater than 850 nm.

The detector 216 can be disposed in any suitable location within the housing 202 of the system 200 or outside of the housing (e.g., on the second major surface 212 of the substrate 204). In one or more embodiments, the detector 216 is disposed adjacent the first major surface 210 of the substrate 204. In one or more embodiments, the detector 216 can be disposed on the first major surface 210 of the substrate 204 using any suitable technique or techniques as shown in FIG. 9. In such embodiments, the detecting surface 230 can be connected to the first major surface 210 of the substrate 204 using any suitable technique. For example, in one or more embodiments, the detecting surface 230 can be disposed on the first major surface 210 of the substrate 204 using an optical coupling layer. Any suitable coupling layer can be utilized. In one or more embodiments, the optical coupling layer can include an optical adhesive. In one or more embodiments, the detector 216 can be electrically connected to an electrode disposed on a carrier. The detector 216 can also be wired bonded from the integrated circuit package 10 to a second electrode on the carrier. The carrier can be designed such that the two electrodes are in a single plane. The carrier can then be bump-bonded to one or more conductors (e.g., conductor 232) disposed on the substrate 204.

The detector 216 can be electrically connected to one or more of the other electronic devices 214 disposed on one or both of the first major surface 210 and second major surface 212 of the substrate 204 or within the housing 202 using any suitable technique or techniques. For example, the detector 216 can be electrically connected to the conductor 232 that is disposed on or within the substrate 204. In one or more embodiments, the conductor 232 can electrically connect the detector 218 to the controller 228 of the electronic devices 214. Any suitable technique or techniques can be utilized to electrically connect the detector 218 to the conductor 232.

The various embodiments of systems described herein can be utilized to determine one or more physiological conditions. Any suitable physiological condition can be determined, e.g., heart rate, arterial blood oxygen level ($SpO_2$), blood flow, fluid volume (e.g., edema), tissue oxygen saturation ($StO_2$), perfusion index (PI), Total Hemoglobin/Hematocrit, Tissue Hemoglobin Concentration Index (THI), venous oxygen saturation (SvO$_2$), ambient light level within a patient, respiration rate, optically interrogated biochemical sensors (e.g., fluorescent or other coatings and materials in contact with tissue), pulse wave velocity (e.g., pulse transit time), etc.

Further, the various embodiments of integrated circuit packages described herein can be manufactured using any suitable technique or techniques. For example, FIGS. 10A-J are various cross-section views of one method 300 of forming integrated circuit package 10. Although described in reference to integrated circuit package 10 of FIGS. 1-2, the method 300 can be utilized to form any suitable integrated circuit package.

Figures 10A, 10B:
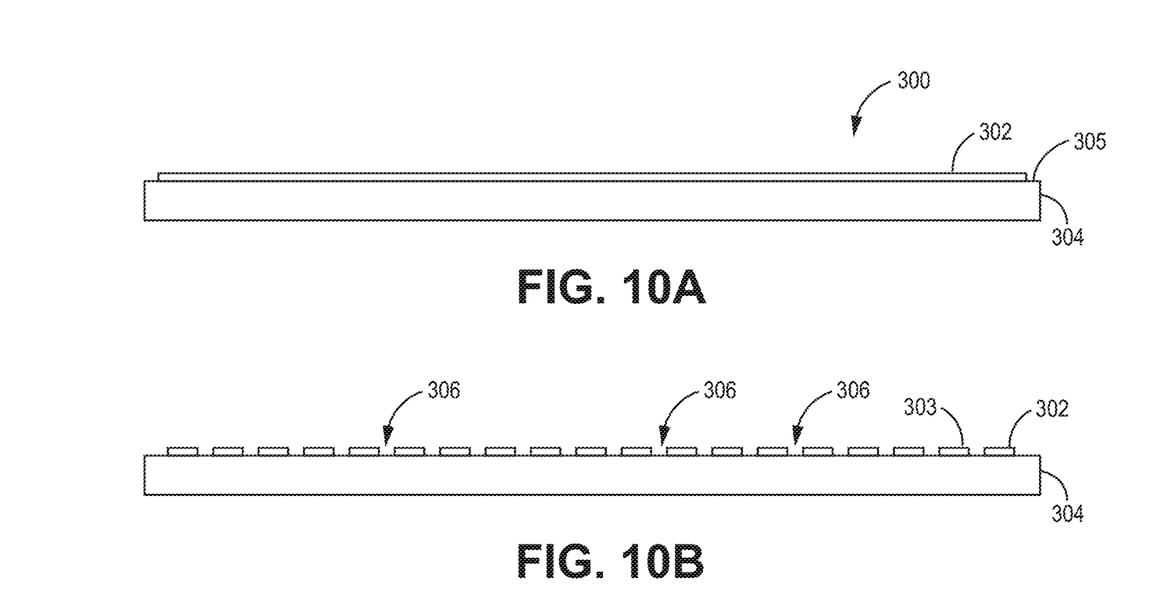
FIG. 10A is a schematic cross-section view of disposing a conductive layer on a major surface of an active die wafer.
FIG. 10B is a schematic cross-section view of patterning the conductive layer to provide a patterned conductive layer.
Figure 10C:
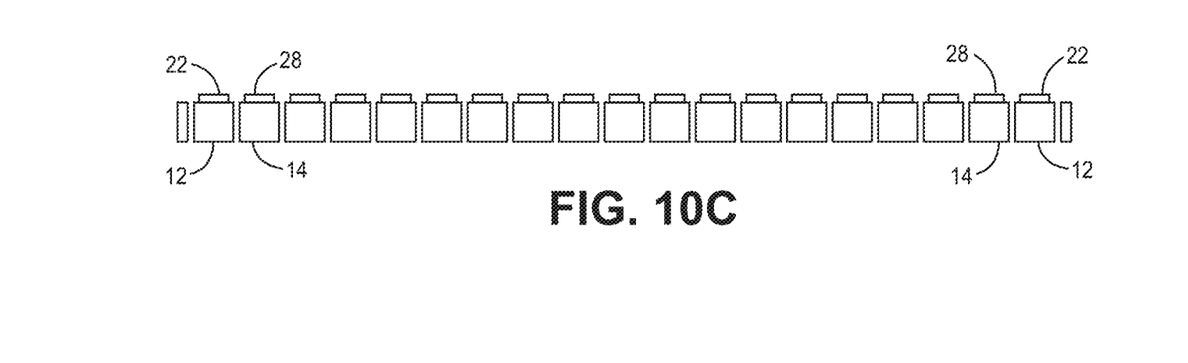
FIG. 10C is a schematic cross-section view of singulating the active die wafer to provide active dies.

As shown in FIG. 10A, a conductive layer 302 can be disposed on a major surface 305 of an active die wafer 304 using any suitable technique or techniques. The conductive layer 302 can be patterned in FIG. 10B to provide a patterned conductive layer 303 on the active die wafer 304. Singulation streets 306 can also be formed in the patterned conductive layer 303 using any suitable technique or techniques. In one or more embodiments, a portion or portions of the conductive layer 302 can be removed to form the patterned conductive layer 303. As shown in FIG. 10C, the active die wafer 304 can be singulated using any suitable technique or techniques to provide individual active dies 308. The active dies 308 can include one or more of the first active die 12 and the second active die 14 of the integrated circuit package 10 of FIGS. 1-2. The first active dies 12 can each be adapted to emit electromagnetic radiation includes a first wavelength, and the second active dies can each be adapted to emit electromagnetic radiation that includes a second wavelength. In one or more embodiments, the first wavelength is different from the second wavelength. Further, the patterned conductive layer 303 of FIG. 10B can be utilized to form the bottom contacts 22 of the first active dies 12 and the bottom contacts 28 of the second active dies 14.

Figure 10D:
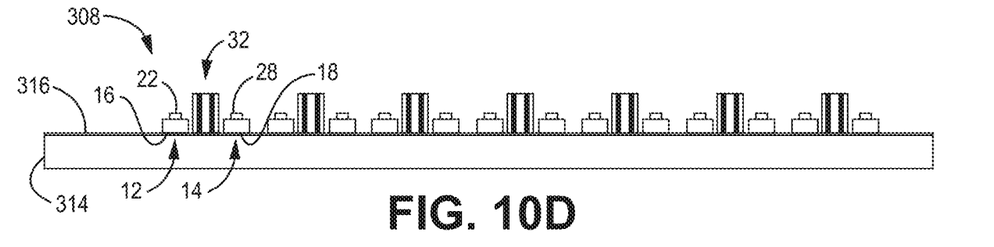
FIG. 10D is a schematic cross-section view of disposing the active dies and via dies on a carrier layer.

As shown in FIG. 10D, the active dies 308 can be disposed on a carrier layer 314 using any suitable technique or techniques. The active dies 308 can be disposed in any suitable arrangement or array on the carrier layer 314. Further, the active dies 308 can be disposed such that the top surfaces 16, 18 of the first and second active dies 12, 14 are disposed on the carrier layer. In one or more embodiments, an optional temporary adhesive layer 316 can be disposed between the active dies 308 and the carrier layer 314. Further, one or more via dies 32 can also be disposed on the carrier layer 314 using any suitable technique or techniques. The via dies 32 can be disposed in any suitable arrangement or array on the carrier layer 314. Further, the via dies 32 can be disposed in any suitable relationship relative to the active dies 308.

Figure 10E:
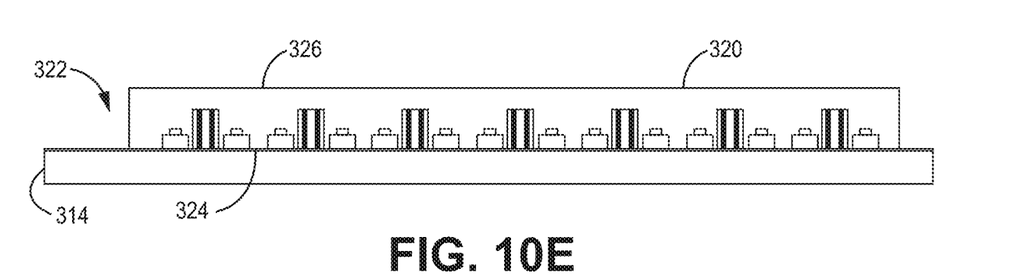
FIG. 10E is a schematic cross-section view of encapsulating the actives dies and the via dies to provide a compression molded wafer.
Figure 10F:
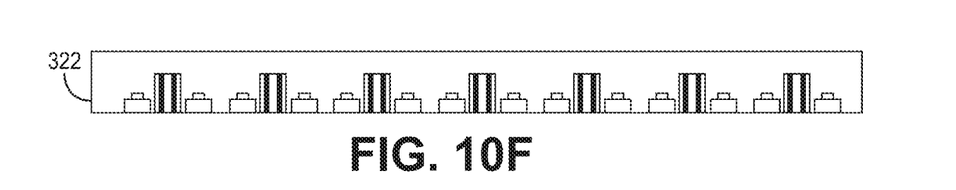
FIG. 10F is a schematic cross-section view of removing the carrier layer from the compression molded wafer.

As shown in FIG. 10E, an encapsulant 320 can be disposed over one or more of the active dies 308 and the via dies 32 using any suitable technique or techniques. In one or more embodiments, the encapsulant 320 can be molded onto the active dies 308 and the via dies 32 as well as one or more portions of the carrier layer 314. In one or more embodiments, the encapsulant 320 is compression molded to provide a compression molded wafer 322 that includes a top surface 324 and a bottom surface 326, where the top surface is disposed on the carrier layer 314. In FIG. 10F, the carrier layer 314 can be removed from the compression molded wafer 322 using any suitable technique or techniques.

Figure 10G:
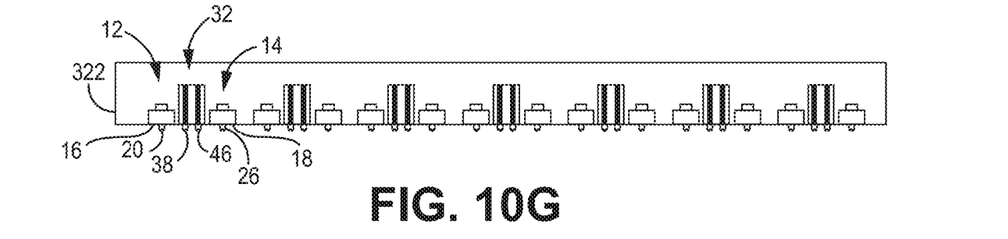
FIG. 10G is a schematic cross-section view of disposing one or more top contacts on a top surface of each of the active dies and via dies.
Figure 10H:
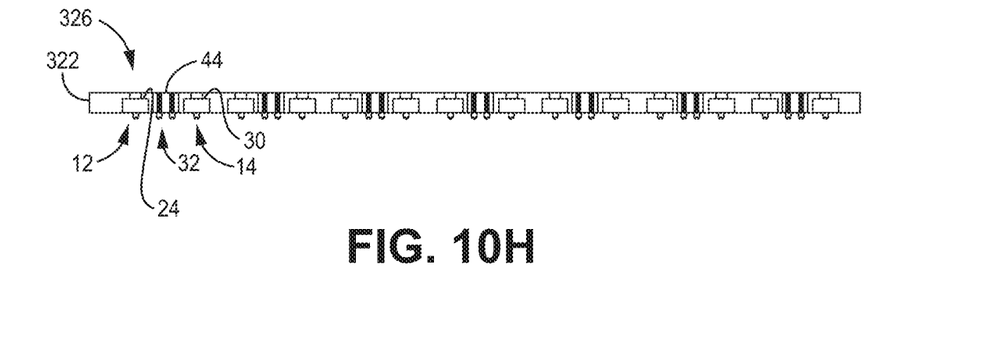
FIG. 10H is a schematic cross-section view of planarizing a top surface of the compression molded wafer.

As shown in FIG. 10G, one or more top contacts 20 can be disposed on the top surfaces 16 of the first active dies 12, and one or more top contacts 26 can be disposed on the top surfaces 18 of the second active dies 14 using any suitable technique or techniques. In one or more embodiments, the top contacts 20, 26 can include solder bumps. One or more top contacts 38, 46 can also be disposed on each via die 32 using any suitable technique or techniques. Further, as shown in FIG. 10H, the bottom surface 326 of the compression molded wafer 322 can be planarized using any suitable technique or techniques to expose the bottom surfaces 24, 30, 44 of each of the first and second active dies 12, 14 and the via dies 32. In one or more embodiments, the compression molded wafer 322 can be planarized using any suitable grinding techniques to expose the pattern conductive layer bottom surfaces 24, 30, 44 of the first and second active dies 12, 14 and the via dies 32.

Figure 10I:
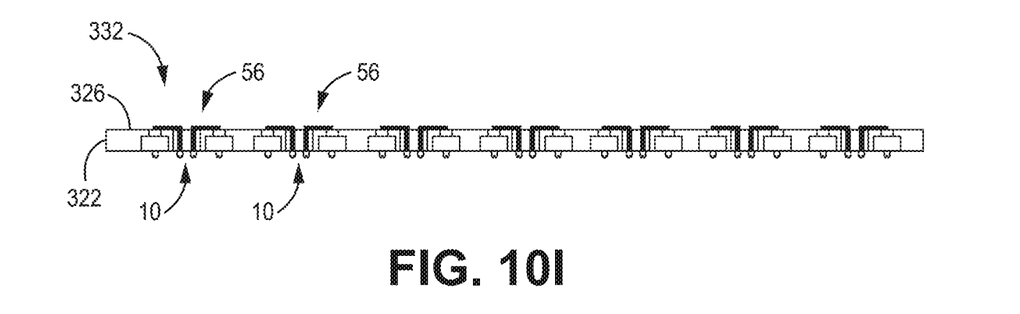
FIG. 10I is a schematic cross-section view of disposing a patterned conductive layer on a bottom surface of the compression molded wafer.
Figure 10J:
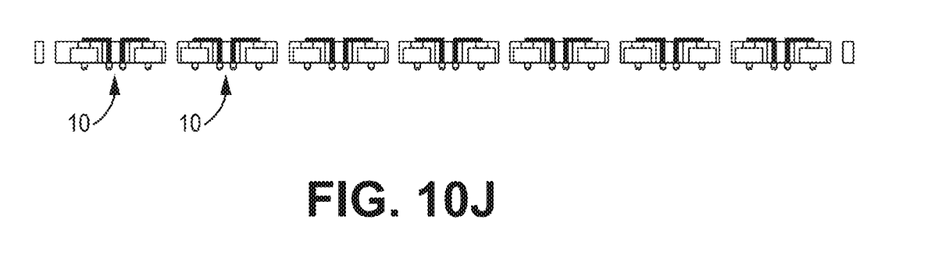
FIG. 10J is a schematic cross-section view of singulating the compression molded wafer.

As shown in FIG. 10I, a patterned conductive layer 332 can be disposed on the bottom surface 326 of the compression molded wafer 322 using any suitable technique or techniques to provide the patterned conductive layer 56 for each integrated circuit package 10. In FIG. 10J, the compression molded wafer 322 can be singulated using any suitable technique or techniques to provide individual integrated circuit packages 10.

All references and publications cited herein are expressly incorporated herein by reference in their entirety into this disclosure, except to the extent they may directly contradict this disclosure. Illustrative embodiments of this disclosure are discussed, and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A hermetically-sealed system comprising:
   an integrated circuit package comprising:
      first and second active dies, wherein the first active die is adapted to emit electromagnetic radiation from a top surface that comprises a first wavelength and the second active die is adapted to emit electromagnetic radiation from a top surface that comprises a second wavelength different from the first wavelength, wherein each of the first and second active dies comprises a top contact disposed on the top surface of each of the first and second active dies and a bottom contact disposed on a bottom surface of each of the first and second active dies; and
      a via die comprising first and second vias that each extends between a top contact disposed on a top surface of the via die and a bottom contact disposed on a bottom surface of the via die, wherein the bottom contact of the first active die is electrically connected to the bottom contact of the first via of the via die and the bottom contact of the second active die is electrically connected to the bottom contact of the second via of the via die;
   a housing comprising an inner surface and an outer surface; and
   a dielectric substrate hermetically sealed to the housing, wherein the substrate comprises a first major surface and a second major surface;
   wherein the integrated circuit package is disposed inside the housing and on the first major surface of the substrate such that at least a portion of the electromagnetic radiation emitted by each of the first and second active dies is transmitted through the first and second major surfaces of the substrate.

2. The system of claim 1, further comprising a detector disposed on the first major surface of the substrate and adapted to detect at least a portion of the electromagnetic radiation transmitted through the first and second major surfaces of the substrate by the first and second active dies of the integrated circuit package.

3. The system of claim 1, wherein the substrate is substantially transmissive to light having a wavelength of at least 200 nm and no greater than 10,000 nm.

4. The system of claim 1, further comprising a patterned conductive layer disposed on the first major surface of the substrate, wherein the first and second active dies and the via die of the integrated circuit package are electrically connected to the patterned conductive layer.

5. The system of claim 1, further comprising a second detector disposed on the first major surface of the substrate, wherein the detector is adapted to detect electromagnetic radiation emitted by the first active die and the second detector is adapted to detect electromagnetic radiation emitted by the second active die.

6. The system of claim 4, wherein the integrated circuit package further comprises solder bumps disposed on the top contact of each of the first and second active dies and the via die, wherein the solder bumps are electrically connected to the first and second active dies, the via die and the patterned conductive layer.

7. The system of claim 1, wherein the integrated circuit package further comprises third, fourth, and fifth active dies, wherein the third active die is adapted to emit electromagnetic radiation from a top surface that comprises a third wavelength, the fourth active die is adapted to emit electromagnetic radiation from a top surface that comprises a fourth wavelength, and the fifth active die is adapted to emit electromagnetic radiation from a top surface of the fifth active die that comprises a fifth wavelength;
wherein the bottom contact of each of the third, fourth, and fifth active dies is electrically connected to bottom contacts of third, fourth, and fifth vias respectively of the via die.

8. The system of claim 1, wherein the first and second active dies and the via die are disposed in a molded encapsulant.

9. The system of claim 8, wherein the integrated circuit package further comprises a patterned conductive layer disposed on the bottom surfaces of the first and second active dies and the via die, wherein the patterned conductive layer electrically connects the bottom contact of the first active die to the bottom contact of the first via of the via die and the bottom contact of the second active die to the bottom contact of the second via of the via die.

10. The system of claim 8, wherein the encapsulant is disposed between the first and second active dies and the via die.

11. The system of claim 1, wherein each of the first and second active dies of the integrated circuit package comprises an aperture disposed on the top surface of the die, wherein the electromagnetic radiation emitted by each of the first and second active dies is directed through the respective aperture.

12. The system of claim 1, further comprising a power source disposed at least partially within the housing and electrically connected to the integrated circuit package.

13. The system of claim 1, further comprising a controller disposed within the housing and electrically connected to the integrated circuit package.

14. The system of claim 2, wherein the detector is adapted to detect visible light having a wavelength of at least 350 nm and no greater than 850 nm.

15. The system of claim 1, wherein the substrate is hermetically sealed to the housing by a laser bond.

16. The system of claim 1, wherein at least one of the first and second active dies comprises a light emitting diode.

17. The system of claim 1, wherein at least one of the first and second active dies comprises a vertical-cavity surface-emitting laser.

18. The system of claim 1, further comprising one or more electronic devices disposed on the first major surface of the dielectric substrate, wherein the integrated circuit package is electrically connected to the one or more electronic devices.

19. The system of claim 18, further comprising a conductor disposed on the first major surface of the substrate, wherein the conductor electrically connects the integrated circuit package to the one or more electronic devices.

20. The system of claim 2, wherein the detector comprises a detecting surface that is disposed on the first major surface of the dielectric substrate using an optical coupling layer.

* * * * *